United States Patent
Wang et al.

(10) Patent No.: US 12,222,264 B2
(45) Date of Patent: Feb. 11, 2025

(54) ACCELERATED LOADING ROAD-TESTING DEVICE

(71) Applicants: Southern Marine Science and Engineering Guangdong Laboratory (Zhuhai), Zhuhai (CN); Sun Yat-sen University, Guangzhou (CN)

(72) Inventors: Fuming Wang, Guangzhou (CN); Chengchao Guo, Guangzhou (CN); Haibo Wang, Guangzhou (CN); Dingfeng Cao, Xingang Xi Road (CN)

(73) Assignees: Sun Yat-sen University (CN); Southern Marine Science and Engineering Guandgong Laboratory (Zhuhai) (CN)

( * ) Notice: Subject to any disclaimer, the term of this patent is extended or adjusted under 35 U.S.C. 154(b) by 430 days.

(21) Appl. No.: 17/659,998

(22) Filed: Apr. 20, 2022

(65) Prior Publication Data
US 2023/0236090 A1 Jul. 27, 2023

(30) Foreign Application Priority Data
Jan. 27, 2022 (CN) .......................... 202210102350.3

(51) Int. Cl.
*G01M 99/00* (2011.01)
*G01M 7/08* (2006.01)
(Continued)

(52) U.S. Cl.
CPC ............ *G01M 99/007* (2013.01); *G01N 3/08* (2013.01); *G01M 7/08* (2013.01); *G01N 3/02* (2013.01);
(Continued)

(58) Field of Classification Search
CPC .......... G01M 99/07; G01M 7/08; G01N 3/08; G01N 3/02; G01N 3/12; G01N 2203/0222; G01N 2203/0242; G01N 33/42
See application file for complete search history.

(56) References Cited

U.S. PATENT DOCUMENTS

2012/0297889 A1* 11/2012 Yngve .................... A43D 1/08
73/818

FOREIGN PATENT DOCUMENTS

| CN | 1392400 A | 1/2003 |
| CN | 103616294 A | 3/2014 |

(Continued)

OTHER PUBLICATIONS

Office Action dated Sep. 26, 2023 in relating Chinese application No. 202210102350.3.

*Primary Examiner* — Jonathan M Dunlap
(74) *Attorney, Agent, or Firm* — Haynes and Boone, LLP (57) ABSTRACT

An accelerated loading road-testing system includes a plurality of loading mechanisms that are sequentially arranged along a first direction. The loading mechanism includes a supporting frame, a sliding assembly, and a loading assembly. The supporting frame includes a horizontal supporting beam disposed along a second direction. The sliding assembly is slidable on the horizontal supporting beam along the second direction. The loading assembly includes a telescopic cylinder and a loading head. A first end of the telescopic cylinder is hinged to the sliding assembly, the second end of the telescopic cylinder is securely connected to the loading head, the telescopic cylinder is configured to drive the loading head to move along the third direction, the loading head is configured to interact with a road surface to be tested in order to adjust an angle between the telescopic cylinder and the sliding assembly and is configured to
(Continued)

always apply a load to a road surface to be tested in a direction perpendicular to the road surface to be tested.

17 Claims, 3 Drawing Sheets

(51) Int. Cl.
    *G01N 3/02*     (2006.01)
    *G01N 3/08*     (2006.01)
    *G01N 3/12*     (2006.01)
    *G01N 33/42*     (2006.01)

(52) U.S. Cl.
    CPC ............... *G01N 3/12* (2013.01); *G01N 33/42* (2013.01); *G01N 2203/0222* (2013.01); *G01N 2203/0242* (2013.01)

(56) References Cited

FOREIGN PATENT DOCUMENTS

| | | | | |
|---|---|---|---|---|
| CN | 206862804 U | | 1/2018 | |
| CN | 208039328 U | | 11/2018 | |
| CN | 109030216 A | * | 12/2018 | |
| CN | 209198223 U | | 8/2019 | |
| CN | 209280470 U | | 8/2019 | |
| CN | 209699090 U | * | 11/2019 | |
| CN | 111678771 A | * | 9/2020 | ............. G01N 17/00 |
| CN | 111982656 A | * | 11/2020 | ........... G01N 17/002 |
| CN | 113203648 A | * | 8/2021 | ........... G01N 17/002 |
| CN | 113311107 A | * | 8/2021 | ............... G01B 5/02 |
| CN | 215374885 U | | 12/2021 | |
| KR | 101654811 B1 | | 9/2016 | |

\* cited by examiner

ACCELERATED LOADING ROAD-TESTING DEVICE

CROSS-REFERENCE TO RELATED APPLICATION(S)

This application claims priority to Chinese Patent Application No. 202210102350.3 filed Jan. 27, 2022, the disclosure of which is incorporated herein by reference in its entirety.

TECHNICAL FIELD

The present disclosure relates to the technical field of traffic engineering and, in particular, an accelerated loading road-testing device.

BACKGROUND

Since the public road and the railroad are under the action of the coupling effect of the long-term traffic load and the complex environment such as soil, rock, and ocean dynamics, engineering infrastructure disasters are led to occur frequently. For example, during the long-term operation of the underground tunnel structure, under the coupling effect of the vehicle cyclic load and the environment, due to longitudinal uneven settlement and lateral convergent deformation, water leakage, lining cracking, joint opening, excessive deformation, and other disasters are caused, which seriously endangers the tunnel structure and the driving safety. The disaster prevention and mitigation problems of various major infrastructures, such as municipal infrastructure, transportation, water conservancy, military infrastructure, and the like, represented by the underground tunnel structure are becoming more and more prominent. Research on the theoretical system, basic theory, and key technologies of disaster prevention and mitigation under the coupling effect of alternating loads and soil, rock, marine dynamics and other environments is carried out, and the disaster prevention and mitigation has become a major problem facing the engineering infrastructure and needs to be solved urgently. The accelerated loading road-testing device is a scientific research system through which rapid indoor tests on the long-term service performance of the engineering infrastructure can be carried out. Theoretical and technical research on disaster prevention and control of the engineering infrastructure based on the system is significant and urgent.

The accelerated loading road-testing device in the related art generally uses a hydraulic cylinder as loading power. The magnitude of the maximum load of the hydraulic cylinder cannot reach the magnitude of the load applied by the heavy truck, the plane or the train to the road surface. There is an urgent need for an accelerated loading road-testing device that can implement a heavy load.

SUMMARY

The present disclosure provides an accelerated loading road-testing device, so as to solve the problem that the accelerated loading road-testing device in the related art cannot achieve a heavy load.

The present disclosure provides an accelerated loading road-testing device. The accelerated loading road-testing device includes a plurality of loading mechanisms. The plurality of loading mechanisms are sequentially arranged along a first direction. Each of the loading mechanisms includes a supporting frame, a sliding assembly, and a loading assembly. The supporting frame includes a horizontal supporting beam, the horizontal supporting beam is disposed along a second direction, and has a sliding state in which the horizontal supporting beam slides along the third direction, and a static state in which the horizontal supporting beam is static. The sliding assembly is disposed on the horizontal supporting beam, and slidable on the horizontal supporting beam along the second direction. The loading assembly includes a telescopic cylinder and a loading head, where a first end of the telescopic cylinder is hinged to the sliding assembly, a second end of the telescopic cylinder is securely connected to the loading head, the telescopic cylinder is configured to drive the loading head to move along the third direction, the loading head is configured to interact with a road surface to be tested in order to adjust an angle between the telescopic cylinder and the sliding assembly and is configured to always apply a load to a road surface to be tested in a direction perpendicular to the road surface to be tested, and the first direction, the second direction and the third direction are perpendicular to one another.

REFERENCE LIST 100 road surface to be tested
1 supporting frame
11 horizontal supporting beam
12 upright column
13 third driver
2 sliding assembly
21 slidable sleeve
221 driving motor
222 rack
223 reducer
224 gear
23 hinging lug
3 loading assembly
31 telescopic cylinder
32 loading head
321 loading plate
3211 sliding groove
322 second driver
323 rubber tire
3231 groove
324 securing plate
3241 protruded sliding rail
325 steel rail
33 force sensor
200 loading mechanism
300 environment stimulation system
301 temperature adjustment module
302 humidity adjustment module
303 optical radiation adjustment module
304 spray module

DETAILED DESCRIPTION

The technical solution of the present disclosure is described clearly and completely below in conjunction with drawings. Apparently, the described embodiments are part, not all, of embodiments of the present disclosure.

In the description of the present disclosure, it is to be noted that orientations or position relations indicated by terms such as "center", "upper", "lower", "left", "right", "vertical", "horizontal", "in", and "out" are based on the drawings. These orientations or position relations are intended only to facilitate and simplify the description of the present disclosure, but not to indicate or imply that a device or element referred to must have such particular orientations or must be configured or operated in such particular orientations. In addition, terms such as "first" and "second" are used only for the purpose of description, are not to be construed as indicating or implying relative importance. Terms "first position" and "second position" are two different positions. Moreover, when the first feature is described as "on", "above", or "over" the second feature, the first feature is right on, above, or over the second feature or the first feature is obliquely on, above, or over the second feature, or the first feature is simply at a higher level than the second feature. When the first feature is described as "under", "below", or "underneath" the second feature, the first feature is right under, below, or underneath the second feature or the first feature is obliquely under, below, or underneath the second feature, or the first feature is simply at a lower level than the second feature.

In the description of the present disclosure, it is to be noted that unless otherwise expressly specified and limited, the term "mounted", "connected to each other", or "connected" should be construed in a broad sense as securely connected, detachably connected, or integrally connected; mechanically connected or electrically connected; directly connected to each other or indirectly connected to each other via an intermediary; or intra-connected between two components. For those of ordinary skill in the art, meanings of the preceding terms in the present disclosure may be understood based on situations.

The embodiments of the present disclosure are described in detail below, and examples of the embodiments are illustrated in the drawings, where the same or similar reference numerals indicate the same or similar elements or elements having the same or similar functions. The embodiments described below with reference to the drawings are merely exemplary and intended to explain the present disclosure.

As shown in FIGS. 1 to 4, this embodiment provides an accelerated loading road-testing device. The accelerated loading road-testing device includes a plurality of loading mechanisms 200. The plurality of loading mechanisms 200 are sequentially arranged along a first direction. Each of the loading mechanisms 200 includes a supporting frame 1, a sliding assembly 2, and a loading assembly 3. The supporting frame 1 includes a horizontal supporting beam 11. The horizontal supporting beam 11 is disposed along a second direction, and has a sliding state in which the horizontal supporting beam 11 slides along the third direction, and a static state in which the horizontal supporting beam 11 is static. The sliding assembly 2 is disposed on the horizontal supporting beam 11, and slidable on the horizontal supporting beam 11 along the second direction. The loading assembly 3 includes a telescopic cylinder 31 and a loading head 32. A first end of the telescopic cylinder 31 is hinged to the sliding assembly 2, a second end of the telescopic cylinder 31 is securely connected to the loading head 32, the telescopic cylinder 31 is configured to always drive the loading head 32 to move along the third direction, the loading head 32 is configured to interaction with a road surface 100 to be tested in order to adjust an angle between the telescopic cylinder 31 and the sliding assembly 2 and is configured to always apply a load to a road surface 100 to be tested in a direction perpendicular to the road surface 100 to be tested. The first direction, the second direction and the third direction are perpendicular to one another. When the accelerated loading road-testing device is conducting a test, firstly the first direction is configured as the lengthwise direction of the road surface 100 to be tested, the second direction is configured as the width direction of the road surface 100 to be tested, the third direction is configured as the direction substantially perpendicular to the road surface 100 to be tested, and the plurality of the loading mechanism 200 are disposed sequentially along first direction and above the road surface 100 to be tested. A position of the sliding assembly 2 is adjusted, at this time, loading head 32 reaches a position where the road surface 100 to be tested is loaded, then telescopic cylinder 31 extends, since the position of the horizontal supporting beam 11 with respect to the road surface 100 to be tested is fixed, telescopic cylinder 31 applies a loading force on the loading head 32, the loading force acts on the road surface 100 to be tested. When the maximum load applied by the telescopic cylinder 31 is less than the load required by the test, horizontal supporting beam 11 changes from the static state to the sliding state, moves in a direction towards the road surface 100 to be tested, thus further improving the load applied by the loading head 32 to the road surface 100 to be tested, and satisfying a heavy load required by the test. The device solves the problem that the accelerated loading road-testing device in the related art cannot provide a heavy load.

Figure 1:
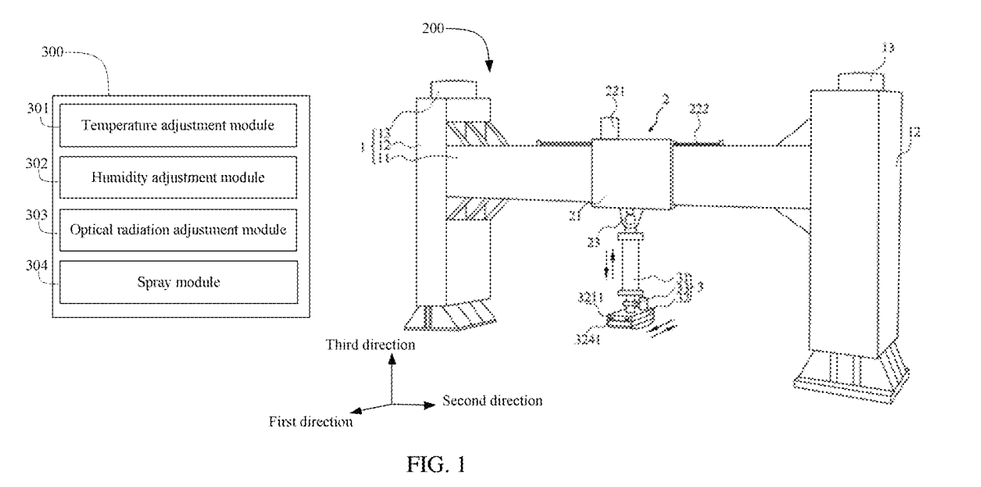
FIG. 1 is a structural view of a loading mechanism according to an embodiment of the present disclosure.

The following refers to how the horizontal supporting beam 11 has a sliding state in which the horizontal supporting beam 11 slides along the third direction, and a static state in which the horizontal supporting beam 11 is static. Optionally, the supporting frame 1 further includes two upright columns 12. The two upright columns 12 are spaced apart along the second direction. Two ends of the horizontal supporting beam 11 are slidably connected to the two upright columns 12 respectively. The supporting frame 1 further includes two third drivers 13. Each of the two third drivers 13 is configured to drive each of the two ends of the horizontal supporting beam 11 to slide with respect to the upright column 12. In this embodiment, each of the third driver 13 is configured to drive each of the two ends of horizontal supporting beam 11 to have the static state and the sliding state. When the load of the telescopic cylinder 31 cannot satisfy a load required by the test, horizontal supporting beam 11 changes from the static state to the sliding state with respect to the road surface 100 to be tested. Further, horizontal supporting beam 11 continues applying load to the loading head 32. Referring to the structure of the third driver 13, the third driver 13 may be a driver with a gear 224 and a rack 222, or a driver with a lead screw and a nut, or a driver with a hydraulic cylinder, or the like.

It is further to be noted that, telescopic cylinder 31 is a hydraulic cylinder. The loading system further includes a storage tank to provide necessary hydraulic oil for the storage tank. In other embodiments, the telescopic cylinder 31 may be an air cylinder.

Optionally, the first end of the telescopic cylinder 31 is rotatable with respect to the sliding assembly 2 merely in a plane where the second direction and the third direction locate. In this embodiment, in some turning path, the road surface may have a lower inner side and a higher outer side. To ensure that the stretching direction of the telescopic cylinder 31 is perpendicular to the road surface 100 to be tested, the angle between the telescopic cylinder 31 and the sliding assembly 2 may be adjusted so as to implement that the stretching direction of the telescopic cylinder 31 is perpendicular to the road surface 100 to be tested.

Optionally, loading assembly 3 further includes a force sensor 33. The force sensor 33 is configured to monitor a force applied by the telescopic cylinder 31 on the loading head 32. In this embodiment, the force sensor 33 transmits, to the controller, the monitored force applied by the telescopic cylinder 31 to the loading head 32. The controller adjusts the operation state of the telescopic cylinder 31 and the third driver according to the magnitude of the load.

Optionally, the sliding assembly 2 includes a slidable sleeve 21, a first driver, and a hinging lug 23. The slidable sleeve 21 is sleeved on the horizontal supporting beam 11 and is slidable along the second direction with respect to the horizontal supporting beam 11. The first driver drives the slidable sleeve 21 to slide along the second direction and with respect to the horizontal supporting beam 11. The first end of the telescopic cylinder 31 is hinged to the slidable sleeve 21 through the hinging lug 23. In this embodiment, the first driver drives the slidable sleeve 21 to move so as to adjust the loading position of the loading head 32. One end of the hinging lug 23 is securely connected to the slidable sleeve 21, the other end of the hinging lug 23 is hinged to the telescopic cylinder 31, and the hinging lug 23 is provided with a locker. The locker can lock the relative position between the hinging lug 23 and the telescopic cylinder 31, and make the telescopic cylinder 31 rotatable relative to the hinging lug 23.

Optionally, the first driver includes a driving motor 221, a reducer 223, a gear 224, and a rack 222. The rack 222 is laid over the horizontal supporting beam 11 along the second direction, the gear 224 is rotatably connected to the slidable sleeve 21, the gear 224 is engaged with the rack 222, and the driving motor 221 is configured to drive, through the reducer 223, the gear 224 to rotate. In this embodiment, the reducer 223 has functions of reducing a rotation speed and increasing a torsional moment. In other embodiments, the first driver may be an assembly including a lead screw and a nut.

Figure 2:
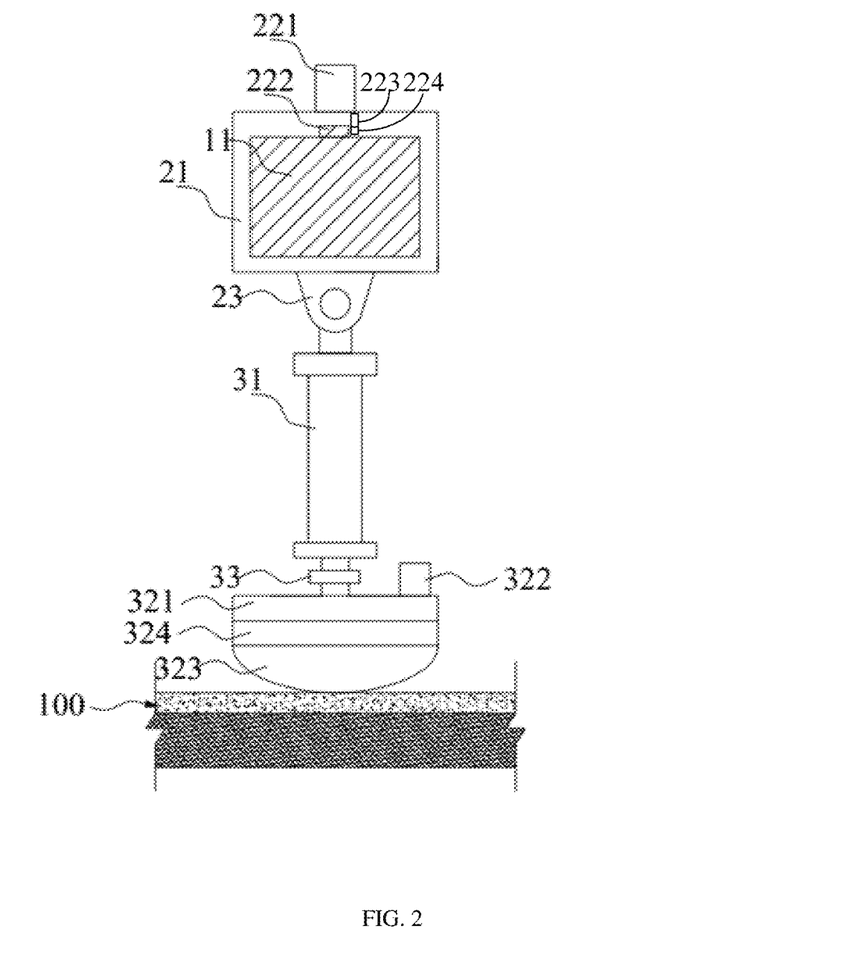
FIG. 2 is a sectional view of a loading mechanism mounted with a rubber tire according to an embodiment of the present disclosure.
Figure 4:
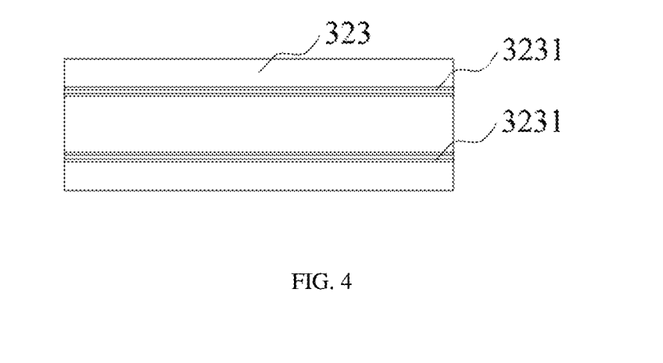
FIG. 4 is a top view of a rubber tire according to an embodiment of the present disclosure.

In a case where a road surface for a normal car to run, or a runway for a plane to fly is needed to be tested through the loading head 32, referring to FIG. 2, optionally, the loading head 32 includes a loading plate 321. The loading plate 321 is securely connected to the second end of the telescopic cylinder 31, and an end surface of the loading plate 321 away from the telescopic cylinder 31 is provided with a sliding groove 3211 along the first direction. The loading head 32 further includes a second driver 322, a rubber tire 323, and a securing plate 324. A surface of the securing plate 324 opposite to the loading plate 321 is provided with a protruded sliding rail 3241. The protruded sliding rail 3241 slidably mates with the sliding groove 3211. The second driver 322 drives the protruded sliding rail 3241 to slide in the sliding groove 3211. The rubber tire 323 is securely connected to the securing plate 324. In this embodiment, the rubber tire 323 simulates real actions of a tire of a car or a plane on the ground. In a case where a normal road surface is needed to be tested, optionally, the rubber tire 323 facing the road surface 100 to be tested is provided with a plurality of grooves 3231 spaced apart along the first direction. The tire pressure of the rubber tire 323 is adjustable. Most of tires used by cars running on a normal road are pneumatic tires. Therefore, in this embodiment, the rubber tire 323 can be inflated to change the tire pressure of the rubber tire 323 so as to simulate a normal tire. Referring to FIG. 4, the side of the rubber tire 323 facing the road surface 100 to be tested is provided with a plurality of grooves 3231 which are spaced apart along the first direction. When the rubber tire 323 is acted by a force directed to the road surface 100 to be tested in a direction perpendicular to the road surface 100 to be tested, the solid rubber layer having grooves 3231 is easier to elastically deform, and thus a force can be reacted on the ground in the second direction. The forces have the same magnitude and opposite directions, and direct to the second direction. Since the securing plate 324 can move relative to the loading plate 321 in the first direction, the rubber tire 323 generates a force along the first direction. The force can simulate grip applied by the tire to the ground when the car moves forwards or backwards.

Figure 3:
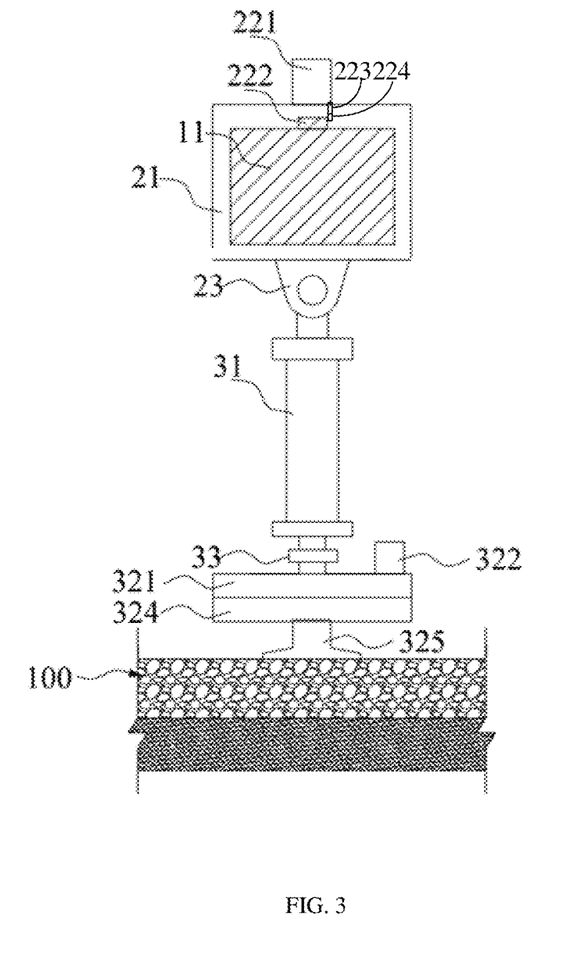
FIG. 3 is a sectional view of a loading mechanism mounted with a steel rail according to an embodiment of the present disclosure.

In a case where the loading head 32 needs to test the high-speed railway ballastless track, referring to FIG. 3, optionally, the loading head 32 includes a loading plate 321. The loading plate 321 is securely connected to the second end of the telescopic cylinder 31. An end surface of the loading plate 321 away from a telescopic cylinder 31 is provided with a sliding groove 3211 along the first direction. The loading head 32 further includes a second driver 322, a steel rail 325 and a securing plate 324. A surface of the securing plate 324 opposite to the loading plate 321 is provided with a protruded sliding rail 3241. The protruded sliding rail 3241 mates with the sliding groove 3211. The second driver 322 drives the protruded sliding rail 3241 to slide in the sliding groove 3211. The steel rail 325 is securely connected to the securing plate 324. In this embodiment, the steel rail 325 is made of stainless steel. In a case where a high-speed loading test on the high-speed railway ballastless track is conducted, since the wheels of the high-speed railway are steel wheels, the steel rail 325 is directly used on the ballastless track to be tested, and the situation where wheels of a high-speed train act on a ballastless track is simulated. The arrangement can improve the reliability of the test. The second driver 322 drives the steel rail 325 to slide along the first direction, and thus grip applied by the train during running can be simulated.

When a test on a runway for a plane to fly is needed to be tested, the steel rail 325 and the securing plate 324 are replaced by a solid rubber layer and a rubber layer securing plate 324. A surface of the rubber layer securing plate 324 facing the loading plate 321 is provided with a protruded sliding rail 3241. The protruded sliding rail 3241 slidably matches with the sliding groove 3211. The second driver 322 drives the protruded sliding rail 3241 to slide in the sliding groove 3211. The solid rubber layer is securely connected to the rubber layer 324. In this embodiment, the solid rubber layer can be configured to simulate a carrier with solid tires.

Optionally, the accelerated loading road-testing device further includes an environment stimulation system 300. The environment stimulation system 300 includes a temperature adjustment module 301, a humidity adjustment module 302, an optical radiation adjustment module 303, and a spray module 304. The temperature adjustment module 301 is configured to adjust an environmental temperature of the road surface 100 to be tested, the humidity adjustment module 302 is configured to adjust environmental humidity of the road surface 100 to be tested, the optical radiation adjustment module 303 is configured to adjust a light radiation intensity of the road surface 100 to be tested, and the spray module 304 is configured to spray water on the road surface 100 to be tested. In this embodiment, the environment stimulation system 300 is mainly configured to simulate more realistic multi-field coupling loading conditions, in many working conditions applied to tunnels, high-speed railways, airports, highways, and the like, so as to achieve more accurate test results, improve test results, and better advance scientific research. Optionally, the humidity adjustment module 300 is configured to adjust an environmental temperature of the road surface 100 to be tested. The temperature field to be applied ranges from −40° C. to 80° C., and the fluctuations ranges between ±2° C. The humidity adjustment module 302 is configured to adjust a environmental humidity of the road surface 100 to be tested. The optical radiation adjustment 303 module simulates a sunlight radiation intensity of the road surface 100 to be tested, and the sunlight radiation intensity reaches a radiation ranging from 200 W/m$^2$ to 1100 W/m$^2$. The spray module 304 is configured to simulate the situation where it rains and the rain acts on the road surface 100 to be tested, and the achievable rain intensity is 0.25 mm/h, 1.0 mm/h, 4.0 mm/h, 16 mm/h, 50 mm/h and greater than 50 mm/h, where mm/h means one millimeter of rainfall per hour.

Optionally, the accelerated loading road-testing device further includes a controlling system. The controlling system is separately connected to a loading system and a environment stimulation system 300. In this embodiment, the controlling system is configured to control working states of the loading system and the environment stimulation system 300.

The present disclosure provides an accelerated loading road-testing device. The accelerated loading road-testing device includes a plurality of loading mechanisms 200. The plurality of loading mechanisms 200 are arranged along a first direction. The loading mechanism 200 includes a supporting frame, a sliding assembly, and a loading assembly. The supporting frame includes a horizontal supporting beam, the horizontal supporting beam is disposed along a second direction, and has a sliding state in which the horizontal supporting beam slides along the third direction, and a static state in which the horizontal supporting beam is static. The sliding assembly is disposed on the horizontal supporting beam, and slidable on the horizontal supporting beam along the second direction. The loading assembly includes a telescopic cylinder and a loading head, where a first end of the telescopic cylinder is hinged to the sliding assembly, a second end of the telescopic cylinder is securely connected to the loading head, the telescopic cylinder is configured to drive the loading head to move along the third direction, the loading head is configured to interact with a road surface to be tested in order to adjust an angle between the telescopic cylinder and the sliding assembly and always apply a load to a road surface to be tested in a direction perpendicular to the road surface to be tested, and the first direction, the second direction and the third direction are perpendicular to one another. When the accelerated loading road-testing device is conducting a test, firstly the first direction is configured as the lengthwise direction of the road surface to be tested, the second direction is configured as the width direction of the road surface to be tested, the third direction is configured as the direction substantially perpendicular to the road surface to be tested, and the plurality of the loading mechanism are disposed sequentially along first direction and above the road surface to be tested. A position of the sliding assembly is adjusted, at this time, loading head reaches a position where the road surface to be tested is loaded, then telescopic cylinder extends, since the position of the horizontal supporting beam with respect to the road surface to be tested is fixed, telescopic cylinder applies a loading force on the loading head, the loading force acts on the road surface to be tested. When the maximum load applied by the telescopic cylinder is less than the load required by the test, horizontal supporting beam changes from the static state to the sliding state, moves in a direction towards the road surface to be tested, thus further improving the load applied by the loading head to the road surface to be tested, and satisfying a heavy load required by the test. The device solves the problem that the accelerated loading road-testing device in the related art cannot provide a heavy load.

What is claimed is:

1. An accelerated loading road-testing device, comprising a plurality of loading mechanisms, wherein the plurality of loading mechanisms are sequentially arranged along a first direction, wherein each of the plurality of loading mechanisms comprises:
a supporting frame, comprising a horizontal supporting beam, the horizontal supporting beam is disposed along a second direction, and has a sliding state in which the horizontal supporting beam slides along a third direction, and a static state in which the horizontal supporting beam is static;
a sliding assembly, disposed on the horizontal supporting beam, and slidable on the horizontal supporting beam along the second direction;
a loading assembly, comprising a telescopic cylinder and a loading head, wherein a first end of the telescopic cylinder is hinged to the sliding assembly, a second end of the telescopic cylinder is securely connected to the loading head, the telescopic cylinder is configured to drive the loading head to move along the third direction, the loading head is configured to interact with a road surface to be tested in order to adjust an angle between the telescopic cylinder and the sliding assembly and is configured to always apply a load to a road surface to be tested in a direction perpendicular to the road surface to be tested, and the first direction, the second direction and the third direction are perpendicular to one another.

2. The accelerated loading road-testing device of claim 1, wherein in a plane where the second direction and the third direction locate, the first end of the telescopic cylinder is rotatable with respect to the sliding assembly.

3. The accelerated loading road-testing device of claim 2, wherein the sliding assembly comprises a slidable sleeve, a first driver, and a hinging lug, the slidable sleeve is sleeved on the horizontal supporting beam, and is slidable along the second direction with respect to the horizontal supporting beam, the first driver drives the slidable sleeve to slide along the second direction with respect to the horizontal supporting beam, and the first end of the telescopic cylinder is hinged to the slidable sleeve through the hinging lug.

4. The accelerated loading road-testing device of claim 3, wherein the first driver comprises a driving motor, a reducer, a gear and a rack, wherein the rack is laid over the horizontal supporting beam along the second direction, the gear is rotatably connected to the slidable sleeve, the gear is engaged with the rack, and the driving motor is configured to drive, through the reducer, the gear to rotate.

5. The accelerated loading road-testing device of claim 4, wherein the loading head includes a loading plate, wherein the loading plate is securely connected to the second end of the telescopic cylinder, and an end surface of the loading plate away from the telescopic cylinder is provided with a sliding groove along the first direction;

the loading head further comprises a second driver, a rubber tire and a securing plate, a surface of the securing plate opposite to the loading plate is provided with a protruded sliding rail, the protruded sliding rail slidably mates with a sliding groove, the second driver drives the protruded sliding rail to slide in the sliding groove, and the rubber tire is securely connected to the securing plate.

6. The accelerated loading road-testing device of claim 5, wherein a side of the rubber tire away from the securing plate is provided with a plurality of grooves which are spaced apart along the first direction, and a tire pressure of the rubber tire is adjustable.

7. The accelerated loading road-testing device of claim 6, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

8. The accelerated loading road-testing device of claim 5, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

9. The accelerated loading road-testing device of claim 4, wherein the loading head comprises a loading plate, the loading plate is securely connected to the second end of the telescopic cylinder, and an end surface of the loading plate away from the telescopic cylinder is provided with a sliding groove along the first direction;

the loading head further comprises a second driver, a steel rail and a securing plate, wherein a surface of the securing plate opposite to the loading plate is provided with a protruded sliding rail, the protruded sliding rail slidably mates with the sliding groove, the second driver is configured to drive the protruded sliding rail to slide in the sliding groove, and the steel rail is securely connected to the securing plate.

10. The accelerated loading road-testing device of claim 9, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

11. The accelerated loading road-testing device of claim 4, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

12. The accelerated loading road-testing device of claim 3, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

13. The accelerated loading road-testing device of claim 2, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

14. The accelerated loading road-testing device of claim 1, wherein the loading assembly further comprises a force sensor configured to monitor a force applied by the telescopic cylinder on the loading head.

15. The accelerated loading road-testing device of claim 14, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

16. The accelerated loading road-testing device of claim 1, further comprising an environment stimulation system, wherein the environment stimulation system comprises a temperature adjustment module, a humidity adjustment module, an optical radiation adjustment module and a spray module, wherein the temperature adjustment module is configured to adjust an environmental temperature of the road surface to be tested, the humidity adjustment module is configured to adjust environmental humidity of the road surface to be tested, the optical radiation adjustment module is configured to adjust a light radiation intensity of the road surface to be tested, and the spray module is configured to spray water on the road surface to be tested.

17. The accelerated loading road-testing device of claim 16, wherein the supporting frame further comprises two upright columns, wherein the two upright columns are spaced apart along the second direction, two ends of the horizontal supporting beam are slidably connected to the two upright columns respectively;

the supporting frame further comprises two drivers, wherein each of the two drivers drives a respective one of the two ends of the horizontal supporting beam to slide with respect to a respective one of the two upright columns.

* * * * *